(12) United States Patent
Spivey

(10) Patent No.: US 8,241,204 B2
(45) Date of Patent: Aug. 14, 2012

(54) ARTICULATING END CAP

(75) Inventor: James T. Spivey, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 1010 days.

(21) Appl. No.: 12/201,812

(22) Filed: Aug. 29, 2008

(65) Prior Publication Data

US 2010/0056861 A1 Mar. 4, 2010

(51) Int. Cl.
*A61B 1/00* (2006.01)
(52) U.S. Cl. ........ 600/106; 600/104; 600/107; 600/127; 600/129
(58) Field of Classification Search .......... 600/106–107, 600/127, 129
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |

(Continued)

FOREIGN PATENT DOCUMENTS

AU 666310 B2 2/1996

(Continued)

OTHER PUBLICATIONS

International Search Report and Written Opinion for PCT/US2009/054436, Nov. 30, 2009 (15 pages).

(Continued)

*Primary Examiner* — Matthew J Kasztejna

(57) ABSTRACT

Various embodiments of a surgical device and methods of using the surgical device are disclosed. The surgical device may comprise a collar configured to fit over a distal face of an endoscope and rotate about a longitudinal axis of the endoscope. The surgical device may also comprise a flexible, elongate translating mechanism coupled to the collar and extending proximally from the collar. Applying a linear force to the translating mechanism may cause the translating mechanism to exert a rotational force on the collar. In addition, the surgical device may comprise a hollow cap coupled to a distal end of the collar. The cap may be pivotable relative to the collar in a plane parallel to the axis. In addition, the cap may have a first open end configured to face the endoscope and a second open end configured to face distally.

32 Claims, 12 Drawing Sheets

U.S. PATENT DOCUMENTS

| | | |
|---|---|---|
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |

| | | | | | |
|---|---|---|---|---|---|
| 5,441,499 A | 8/1995 | Fritzsch | 5,690,660 A | 11/1997 | Kauker et al. |
| 5,443,463 A | 8/1995 | Stern et al. | 5,695,448 A | 12/1997 | Kimura et al. |
| 5,445,638 A | 8/1995 | Rydell et al. | 5,695,505 A | 12/1997 | Yoon |
| 5,449,021 A | 9/1995 | Chikama | 5,695,511 A | 12/1997 | Cano et al. |
| 5,456,667 A | 10/1995 | Ham et al. | 5,700,275 A | 12/1997 | Bell et al. |
| 5,456,684 A | 10/1995 | Schmidt et al. | 5,702,438 A | 12/1997 | Avitall |
| 5,458,131 A | 10/1995 | Wilk | 5,704,892 A | 1/1998 | Adair |
| 5,458,583 A | 10/1995 | McNeely et al. | 5,709,708 A | 1/1998 | Thal |
| 5,460,168 A | 10/1995 | Masubuchi et al. | 5,716,326 A | 2/1998 | Dannan |
| 5,460,629 A | 10/1995 | Shlain et al. | 5,730,740 A | 3/1998 | Wales et al. |
| 5,462,561 A | 10/1995 | Voda | 5,735,849 A | 4/1998 | Baden et al. |
| 5,465,731 A | 11/1995 | Bell et al. | 5,741,234 A | 4/1998 | Aboul-Hosn |
| 5,467,763 A | 11/1995 | McMahon et al. | 5,741,278 A | 4/1998 | Stevens |
| 5,468,250 A | 11/1995 | Paraschac et al. | 5,741,285 A | 4/1998 | McBrayer et al. |
| 5,470,308 A | 11/1995 | Edwards et al. | 5,746,759 A | 5/1998 | Meade et al. |
| 5,470,320 A | 11/1995 | Tiefenbrun et al. | 5,749,881 A | 5/1998 | Sackier et al. |
| 5,478,347 A | 12/1995 | Aranyi | 5,749,889 A | 5/1998 | Bacich et al. |
| 5,480,404 A | 1/1996 | Kammerer et al. | 5,752,951 A | 5/1998 | Yanik |
| 5,482,054 A | 1/1996 | Slater et al. | 5,755,731 A | 5/1998 | Grinberg |
| 5,484,451 A | 1/1996 | Akopov et al. | 5,766,167 A | 6/1998 | Eggers et al. |
| 5,489,256 A | 2/1996 | Adair | 5,766,170 A | 6/1998 | Eggers |
| 5,496,347 A | 3/1996 | Hashiguchi et al. | 5,766,205 A | 6/1998 | Zvenyatsky et al. |
| 5,499,990 A | 3/1996 | Schülken et al. | 5,769,849 A | 6/1998 | Eggers |
| 5,499,992 A | 3/1996 | Meade et al. | 5,779,701 A | 7/1998 | McBrayer et al. |
| 5,501,692 A | 3/1996 | Riza | 5,779,716 A | 7/1998 | Cano et al. |
| 5,503,616 A | 4/1996 | Jones | 5,779,727 A | 7/1998 | Orejola |
| 5,505,686 A | 4/1996 | Willis et al. | 5,782,859 A | 7/1998 | Nicholas et al. |
| 5,507,755 A | 4/1996 | Gresl et al. | 5,782,866 A | 7/1998 | Wenstrom, Jr. |
| 5,511,564 A | 4/1996 | Wilk | 5,791,022 A | 8/1998 | Bohman |
| 5,514,157 A | 5/1996 | Nicholas et al. | 5,792,113 A | 8/1998 | Kramer et al. |
| 5,522,829 A | 6/1996 | Michalos | 5,792,153 A | 8/1998 | Swain et al. |
| 5,522,830 A | 6/1996 | Aranyi | 5,792,165 A | 8/1998 | Klieman et al. |
| 5,527,321 A | 6/1996 | Hinchliffe | 5,797,835 A | 8/1998 | Green |
| 5,536,248 A | 7/1996 | Weaver et al. | 5,797,928 A | 8/1998 | Kogasaka |
| 5,540,648 A | 7/1996 | Yoon | 5,797,939 A | 8/1998 | Yoon |
| 5,554,151 A | 9/1996 | Hinchliffe | 5,797,941 A | 8/1998 | Schulze et al. |
| 5,555,883 A | 9/1996 | Avitall | 5,803,903 A | 9/1998 | Athas et al. |
| 5,558,133 A | 9/1996 | Bortoli et al. | 5,808,665 A | 9/1998 | Green |
| 5,562,693 A | 10/1996 | Devlin et al. | 5,810,806 A | 9/1998 | Ritchart et al. |
| 5,569,243 A | 10/1996 | Kortenbach et al. | 5,810,849 A | 9/1998 | Kontos |
| 5,569,298 A | 10/1996 | Schnell | 5,810,865 A | 9/1998 | Koscher et al. |
| 5,573,540 A | 11/1996 | Yoon | 5,810,876 A | 9/1998 | Kelleher |
| 5,578,030 A | 11/1996 | Levin | 5,810,877 A | 9/1998 | Roth et al. |
| 5,582,611 A | 12/1996 | Tsuruta et al. | 5,813,976 A | 9/1998 | Filipi et al. |
| 5,582,617 A | 12/1996 | Klieman et al. | 5,814,058 A | 9/1998 | Carlson et al. |
| 5,584,845 A | 12/1996 | Hart | 5,817,061 A | 10/1998 | Goodwin et al. |
| 5,591,179 A | 1/1997 | Edelstein | 5,817,107 A | 10/1998 | Schaller |
| 5,593,420 A | 1/1997 | Eubanks, Jr et al. | 5,817,119 A | 10/1998 | Klieman et al. |
| 5,595,562 A | 1/1997 | Grier | 5,819,736 A | 10/1998 | Avny et al. |
| 5,597,378 A | 1/1997 | Jervis | 5,824,071 A | 10/1998 | Nelson et al. |
| 5,601,573 A | 2/1997 | Fogelberg et al. | 5,827,281 A | 10/1998 | Levin |
| 5,601,588 A | 2/1997 | Tonomura et al. | 5,827,299 A | 10/1998 | Thomason et al. |
| 5,604,531 A | 2/1997 | Iddan et al. | 5,830,231 A | 11/1998 | Geiges, Jr. |
| 5,607,389 A | 3/1997 | Edwards et al. | 5,833,700 A | 11/1998 | Fogelberg et al. |
| 5,607,450 A | 3/1997 | Zvenyatsky et al. | 5,833,703 A | 11/1998 | Manushakian |
| 5,613,975 A | 3/1997 | Christy | 5,843,017 A | 12/1998 | Yoon |
| 5,618,303 A | 4/1997 | Marlow et al. | 5,843,121 A | 12/1998 | Yoon |
| 5,620,415 A | 4/1997 | Lucey et al. | 5,849,022 A | 12/1998 | Sakashita et al. |
| 5,624,399 A | 4/1997 | Ackerman | 5,853,374 A | 12/1998 | Hart et al. |
| 5,624,431 A | 4/1997 | Gerry et al. | 5,855,585 A | 1/1999 | Kontos |
| 5,626,578 A | 5/1997 | Tihon | 5,860,913 A | 1/1999 | Yamaya et al. |
| 5,628,732 A | 5/1997 | Antoon, Jr. et al. | 5,860,995 A | 1/1999 | Berkelaar |
| 5,630,782 A | 5/1997 | Adair | 5,868,762 A | 2/1999 | Cragg et al. |
| 5,643,283 A | 7/1997 | Younker | 5,876,411 A | 3/1999 | Kontos |
| 5,643,292 A | 7/1997 | Hart | 5,882,331 A | 3/1999 | Sasaki |
| 5,643,294 A | 7/1997 | Tovey et al. | 5,882,344 A | 3/1999 | Stouder, Jr. |
| 5,644,798 A | 7/1997 | Shah | 5,893,846 A | 4/1999 | Bales et al. |
| 5,645,083 A | 7/1997 | Essig et al. | 5,893,874 A | 4/1999 | Bourque et al. |
| 5,645,565 A | 7/1997 | Rudd et al. | 5,893,875 A | 4/1999 | O'Connor et al. |
| 5,649,372 A | 7/1997 | Souza | 5,899,919 A | 5/1999 | Eubanks, Jr. et al. |
| 5,653,677 A | 8/1997 | Okada et al. | 5,902,254 A | 5/1999 | Magram |
| 5,653,690 A | 8/1997 | Booth et al. | 5,904,702 A | 5/1999 | Ek et al. |
| 5,653,722 A | 8/1997 | Kieturakis | 5,908,420 A | 6/1999 | Parins et al. |
| 5,662,663 A | 9/1997 | Shallman | 5,911,737 A | 6/1999 | Lee et al. |
| 5,669,875 A | 9/1997 | van Eerdenburg | 5,916,147 A | 6/1999 | Boury |
| 5,681,324 A | 10/1997 | Kammerer et al. | 5,921,993 A | 7/1999 | Yoon |
| 5,681,330 A | 10/1997 | Hughett et al. | 5,921,997 A | 7/1999 | Fogelberg et al. |
| 5,685,820 A | 11/1997 | Riek et al. | 5,922,008 A | 7/1999 | Gimpelson |
| 5,690,656 A | 11/1997 | Cope et al. | 5,925,052 A | 7/1999 | Simmons |

| | | |
|---|---|---|
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,549 A | 9/1999 | Richardson et al. |
| 5,954,720 A | 9/1999 | Wilson et al. |
| 5,954,731 A | 9/1999 | Yoon |
| 5,957,943 A | 9/1999 | Vaitekunas |
| 5,957,953 A | 9/1999 | DiPoto et al. |
| 5,971,995 A | 10/1999 | Rousseau |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,989,182 A | 11/1999 | Hori et al. |
| 5,993,447 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,634 A | 2/2000 | Wu et al. |
| 6,033,399 A | 3/2000 | Gines |
| 6,036,685 A * | 3/2000 | Mueller .................. 606/15 |
| 6,053,927 A | 4/2000 | Hamas |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,108 A | 7/2000 | McBrayer et al. |
| 6,096,046 A | 8/2000 | Weiss |
| 6,102,926 A | 8/2000 | Tartaglia et al. |
| 6,106,473 A | 8/2000 | Violante et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,159,200 A | 12/2000 | Verdura et al. |
| 6,165,184 A | 12/2000 | Verdura et al. |
| 6,168,570 B1 | 1/2001 | Ferrera |
| 6,168,605 B1 | 1/2001 | Measamer et al. |
| 6,170,130 B1 | 1/2001 | Hamilton et al. |
| 6,179,776 B1 | 1/2001 | Adams et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,214,007 B1 | 4/2001 | Anderson |
| 6,228,096 B1 | 5/2001 | Marchand |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,322,578 B1 | 11/2001 | Houle et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,035 B1 | 3/2002 | Manushakian |
| 6,361,534 B1 | 3/2002 | Chen et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,391,029 B1 | 5/2002 | Hooven et al. |
| 6,402,735 B1 | 6/2002 | Langevin |
| 6,406,440 B1 | 6/2002 | Stefanchik |
| 6,409,733 B1 | 6/2002 | Conlon et al. |
| 6,427,089 B1 | 7/2002 | Knowlton |
| 6,431,500 B1 | 8/2002 | Jacobs et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,543,456 B1 | 4/2003 | Freeman |
| 6,551,270 B1 | 4/2003 | Bimbo et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,286 B1 | 10/2003 | Burbank et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |

| Patent No. | Date | Inventor |
|---|---|---|
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,152,488 B2 | 12/2006 | Hedrich et al. |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francese et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |

| | | |
|---|---|---|
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,674,259 B2 | 3/2010 | Shadduck |
| 7,713,270 B2 | 5/2010 | Suzuki |
| 7,736,374 B2 | 6/2010 | Vaughan et al. |
| 7,744,615 B2 | 6/2010 | Couture |
| 7,758,577 B2 | 7/2010 | Nobis et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,780,691 B2 * | 8/2010 | Stefanchik .................. 606/170 |
| 7,794,409 B2 * | 9/2010 | Damarati ..................... 600/565 |
| 7,794,475 B2 | 9/2010 | Hess et al. |
| 7,828,186 B2 | 11/2010 | Wales |
| 7,837,615 B2 | 11/2010 | Le et al. |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,887 B2 | 3/2011 | Rimbaugh et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,931,624 B2 | 4/2011 | Smith et al. |
| 7,945,332 B2 | 5/2011 | Schechter |
| 7,947,000 B2 | 5/2011 | Vargas et al. |
| 7,955,298 B2 | 6/2011 | Carroll et al. |
| 7,963,975 B2 | 6/2011 | Criscuolo |
| 7,988,685 B2 | 8/2011 | Ziaie et al. |
| 8,075,587 B2 | 12/2011 | Ginn |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |

| | | | | | | |
|---|---|---|---|---|---|---|
| 2004/0249394 A1 | 12/2004 | Morris et al. | | 2006/0025781 A1 | 2/2006 | Young et al. |
| 2004/0249443 A1 | 12/2004 | Shanley et al. | | 2006/0025812 A1 | 2/2006 | Shelton et al. |
| 2005/0004515 A1 | 1/2005 | Hart et al. | | 2006/0025819 A1 | 2/2006 | Nobis et al. |
| 2005/0033265 A1 | 2/2005 | Engel et al. | | 2006/0036267 A1 | 2/2006 | Saadat et al. |
| 2005/0033277 A1 | 2/2005 | Clague et al. | | 2006/0041188 A1 | 2/2006 | Dirusso et al. |
| 2005/0033319 A1 | 2/2005 | Gambale et al. | | 2006/0058581 A1* | 3/2006 | Hanke ............................ 600/109 |
| 2005/0033333 A1 | 2/2005 | Smith et al. | | 2006/0058582 A1 | 3/2006 | Maahs et al. |
| 2005/0043690 A1 | 2/2005 | Todd | | 2006/0058776 A1 | 3/2006 | Bilsbury |
| 2005/0049616 A1 | 3/2005 | Rivera et al. | | 2006/0069396 A1 | 3/2006 | Meade et al. |
| 2005/0065397 A1 | 3/2005 | Saadat et al. | | 2006/0069424 A1 | 3/2006 | Acosta et al. |
| 2005/0065517 A1 | 3/2005 | Chin | | 2006/0069425 A1 | 3/2006 | Hillis et al. |
| 2005/0070754 A1 | 3/2005 | Nobis et al. | | 2006/0074413 A1 | 4/2006 | Behzadian |
| 2005/0070763 A1 | 3/2005 | Nobis et al. | | 2006/0079890 A1 | 4/2006 | Guerra |
| 2005/0070764 A1 | 3/2005 | Nobis et al. | | 2006/0089528 A1 | 4/2006 | Tartaglia et al. |
| 2005/0080413 A1 | 4/2005 | Canady | | 2006/0095031 A1 | 5/2006 | Ormsby |
| 2005/0085693 A1 | 4/2005 | Belson et al. | | 2006/0095060 A1 | 5/2006 | Mayenberger et al. |
| 2005/0085832 A1 | 4/2005 | Sancoff et al. | | 2006/0100687 A1 | 5/2006 | Fahey et al. |
| 2005/0090837 A1 | 4/2005 | Sixto, Jr. et al. | | 2006/0106423 A1 | 5/2006 | Weisel et al. |
| 2005/0090838 A1 | 4/2005 | Sixto, Jr. et al. | | 2006/0111209 A1 | 5/2006 | Hinman et al. |
| 2005/0101837 A1 | 5/2005 | Kalloo et al. | | 2006/0111210 A1 | 5/2006 | Hinman, IV |
| 2005/0101838 A1 | 5/2005 | Camillocci et al. | | 2006/0111704 A1 | 5/2006 | Brenneman et al. |
| 2005/0107663 A1 | 5/2005 | Saadat et al. | | 2006/0129166 A1 | 6/2006 | Lavelle |
| 2005/0107664 A1 | 5/2005 | Kalloo et al. | | 2006/0135962 A1 | 6/2006 | Kick et al. |
| 2005/0110881 A1 | 5/2005 | Glukhovsky et al. | | 2006/0135971 A1 | 6/2006 | Swanstrom et al. |
| 2005/0113847 A1 | 5/2005 | Gadberry et al. | | 2006/0135984 A1 | 6/2006 | Kramer et al. |
| 2005/0119613 A1 | 6/2005 | Moenning et al. | | 2006/0142644 A1 | 6/2006 | Mulac et al. |
| 2005/0124855 A1 | 6/2005 | Jaffe et al. | | 2006/0142652 A1 | 6/2006 | Keenan |
| 2005/0125010 A1 | 6/2005 | Smith et al. | | 2006/0142790 A1 | 6/2006 | Gertner |
| 2005/0131279 A1 | 6/2005 | Boulais et al. | | 2006/0142798 A1 | 6/2006 | Holman et al. |
| 2005/0131457 A1 | 6/2005 | Douglas et al. | | 2006/0149131 A1 | 7/2006 | Or |
| 2005/0137454 A1 | 6/2005 | Saadat et al. | | 2006/0149132 A1 | 7/2006 | Iddan |
| 2005/0143647 A1 | 6/2005 | Minai et al. | | 2006/0149135 A1 | 7/2006 | Paz |
| 2005/0143690 A1 | 6/2005 | High | | 2006/0161190 A1 | 7/2006 | Gadberry et al. |
| 2005/0143774 A1 | 6/2005 | Polo | | 2006/0167416 A1 | 7/2006 | Mathis et al. |
| 2005/0143803 A1 | 6/2005 | Watson et al. | | 2006/0167482 A1 | 7/2006 | Swain et al. |
| 2005/0149087 A1 | 7/2005 | Ahlberg et al. | | 2006/0178560 A1 | 8/2006 | Saadat et al. |
| 2005/0149096 A1 | 7/2005 | Hilal et al. | | 2006/0183975 A1 | 8/2006 | Saadat et al. |
| 2005/0159648 A1 | 7/2005 | Freed | | 2006/0184161 A1 | 8/2006 | Maahs et al. |
| 2005/0165272 A1 | 7/2005 | Okada et al. | | 2006/0189844 A1 | 8/2006 | Tien |
| 2005/0165378 A1 | 7/2005 | Heinrich et al. | | 2006/0189845 A1 | 8/2006 | Maahs et al. |
| 2005/0165411 A1 | 7/2005 | Orban, III | | 2006/0190027 A1 | 8/2006 | Downey |
| 2005/0165429 A1 | 7/2005 | Douglas et al. | | 2006/0195084 A1 | 8/2006 | Slater |
| 2005/0182429 A1 | 8/2005 | Yamanouchi | | 2006/0200005 A1 | 9/2006 | Bjork et al. |
| 2005/0192478 A1 | 9/2005 | Williams et al. | | 2006/0200169 A1 | 9/2006 | Sniffin |
| 2005/0192598 A1 | 9/2005 | Johnson et al. | | 2006/0200170 A1 | 9/2006 | Aranyi |
| 2005/0192602 A1 | 9/2005 | Manzo | | 2006/0200199 A1 | 9/2006 | Bonutti et al. |
| 2005/0192654 A1 | 9/2005 | Chanduszko et al. | | 2006/0217665 A1 | 9/2006 | Prosek |
| 2005/0209624 A1 | 9/2005 | Vijay | | 2006/0217697 A1 | 9/2006 | Lau et al. |
| 2005/0215858 A1 | 9/2005 | Vail, III | | 2006/0217742 A1 | 9/2006 | Messerly et al. |
| 2005/0216050 A1 | 9/2005 | Sepetka et al. | | 2006/0217743 A1 | 9/2006 | Messerly et al. |
| 2005/0228406 A1 | 10/2005 | Bose | | 2006/0229639 A1 | 10/2006 | Whitfield |
| 2005/0234297 A1* | 10/2005 | Devierre et al. ............... 600/153 | | 2006/0229640 A1 | 10/2006 | Whitfield |
| 2005/0250983 A1 | 11/2005 | Tremaglio et al. | | 2006/0237022 A1 | 10/2006 | Chen et al. |
| 2005/0250990 A1 | 11/2005 | Le et al. | | 2006/0237023 A1 | 10/2006 | Cox et al. |
| 2005/0250993 A1 | 11/2005 | Jaeger | | 2006/0241570 A1 | 10/2006 | Wilk |
| 2005/0251166 A1 | 11/2005 | Vaughan et al. | | 2006/0247576 A1 | 11/2006 | Poncet |
| 2005/0251176 A1 | 11/2005 | Swanstrom et al. | | 2006/0247673 A1 | 11/2006 | Voegele et al. |
| 2005/0261674 A1 | 11/2005 | Nobis et al. | | 2006/0253004 A1 | 11/2006 | Frisch et al. |
| 2005/0267492 A1 | 12/2005 | Poncet et al. | | 2006/0253039 A1 | 11/2006 | McKenna et al. |
| 2005/0272975 A1 | 12/2005 | McWeeney et al. | | 2006/0258907 A1 | 11/2006 | Stefanchik et al. |
| 2005/0272977 A1 | 12/2005 | Saadat et al. | | 2006/0258908 A1 | 11/2006 | Stefanchik et al. |
| 2005/0273084 A1 | 12/2005 | Hinman et al. | | 2006/0258910 A1 | 11/2006 | Stefanchik et al. |
| 2005/0277945 A1 | 12/2005 | Saadat et al. | | 2006/0258954 A1 | 11/2006 | Timberlake et al. |
| 2005/0277951 A1 | 12/2005 | Smith et al. | | 2006/0258955 A1 | 11/2006 | Hoffman et al. |
| 2005/0277952 A1 | 12/2005 | Arp et al. | | 2006/0259010 A1 | 11/2006 | Stefanchik et al. |
| 2005/0277954 A1 | 12/2005 | Smith et al. | | 2006/0264752 A1 | 11/2006 | Rubinsky et al. |
| 2005/0277955 A1 | 12/2005 | Palmer et al. | | 2006/0264904 A1 | 11/2006 | Kerby et al. |
| 2005/0277956 A1 | 12/2005 | Francese et al. | | 2006/0264930 A1 | 11/2006 | Nishimura |
| 2005/0277957 A1 | 12/2005 | Kuhns et al. | | 2006/0270902 A1 | 11/2006 | Igarashi et al. |
| 2005/0283118 A1 | 12/2005 | Uth et al. | | 2006/0271102 A1 | 11/2006 | Bosshard et al. |
| 2005/0283119 A1 | 12/2005 | Uth et al. | | 2006/0276835 A1 | 12/2006 | Uchida |
| 2005/0288555 A1 | 12/2005 | Binmoeller | | 2006/0281970 A1 | 12/2006 | Stokes et al. |
| 2006/0004406 A1 | 1/2006 | Wehrstein et al. | | 2006/0282106 A1 | 12/2006 | Cole et al. |
| 2006/0004409 A1 | 1/2006 | Nobis et al. | | 2006/0285732 A1 | 12/2006 | Horn et al. |
| 2006/0004410 A1 | 1/2006 | Nobis et al. | | 2006/0287644 A1 | 12/2006 | Inganas et al. |
| 2006/0015009 A1 | 1/2006 | Jaffe et al. | | 2006/0287666 A1 | 12/2006 | Saadat et al. |
| 2006/0020167 A1 | 1/2006 | Sitzmann | | 2006/0293626 A1 | 12/2006 | Byrum et al. |
| 2006/0020247 A1 | 1/2006 | Kagan et al. | | 2007/0002135 A1 | 1/2007 | Glukhovsky |
| 2006/0025654 A1 | 2/2006 | Suzuki et al. | | 2007/0005019 A1 | 1/2007 | Okishige |

| Publication No. | Date | Inventor |
|---|---|---|
| 2007/0010801 A1 | 1/2007 | Chen et al. |
| 2007/0015965 A1 | 1/2007 | Cox et al. |
| 2007/0016255 A1 | 1/2007 | Korb et al. |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0122425 A1 | 5/2007 | Keeler et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0177135 A1* | 7/2008 | Muyari et al. ............... 600/104 |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |

| | | | | | | |
|---|---|---|---|---|---|---|
| 2009/0192344 A1 | 7/2009 | Bakos et al. | | 2011/0245619 A1 | 10/2011 | Holcomb |
| 2009/0192534 A1 | 7/2009 | Ortiz et al. | | 2011/0306971 A1 | 12/2011 | Long |
| 2009/0198231 A1 | 8/2009 | Esser et al. | | 2012/0004502 A1 | 1/2012 | Weitzner et al. |
| 2009/0198253 A1 | 8/2009 | Omori | | | | |

FOREIGN PATENT DOCUMENTS

| | | |
|---|---|---|
| 2009/0216248 A1 8/2009 Uenohara et al. | DE | 3008120 A1 9/1980 |
| 2009/0227828 A1 9/2009 Swain et al. | DE | 4323585 A1 1/1995 |
| 2009/0248055 A1 10/2009 Spivey et al. | DE | 19713797 A1 10/1997 |
| 2009/0281559 A1 11/2009 Swain et al. | DE | 19757056 B4 8/2008 |
| 2009/0287206 A1 11/2009 Jun | DE | 102006027873 B4 10/2009 |
| 2009/0287236 A1 11/2009 Bakos et al. | EP | 0086338 A1 8/1983 |
| 2009/0292164 A1 11/2009 Yamatani | EP | 0268415 A2 10/1988 |
| 2009/0299135 A1 12/2009 Spivey | EP | 0589454 A2 3/1994 |
| 2009/0299143 A1 12/2009 Conlon et al. | EP | 0464479 B1 3/1995 |
| 2009/0299362 A1 12/2009 Long et al. | EP | 0529675 B1 2/1996 |
| 2009/0299385 A1 12/2009 Stefanchik et al. | EP | 0724863 B1 7/1999 |
| 2009/0299406 A1 12/2009 Swain et al. | EP | 0760629 B1 11/1999 |
| 2009/0299409 A1 12/2009 Coe et al. | EP | 0818974 B1 7/2001 |
| 2009/0306658 A1 12/2009 Nobis et al. | EP | 1281356 A2 2/2003 |
| 2009/0306683 A1 12/2009 Zwolinski et al. | EP | 0947166 B1 5/2003 |
| 2009/0322864 A1 12/2009 Karasawa et al. | EP | 0836832 B1 12/2003 |
| 2009/0326561 A1 12/2009 Carroll, II et al. | EP | 1402837 A1 3/2004 |
| 2010/0010294 A1 1/2010 Conlon et al. | EP | 0744918 B1 4/2004 |
| 2010/0010298 A1 1/2010 Bakos et al. | EP | 0931515 B1 8/2004 |
| 2010/0010299 A1 1/2010 Bakos et al. | EP | 0941128 81 10/2004 |
| 2010/0010303 A1 1/2010 Bakos | EP | 1411843 B1 10/2004 |
| 2010/0010510 A1 1/2010 Stefanchik | EP | 1150614 B1 11/2004 |
| 2010/0010511 A1 1/2010 Harris et al. | EP | 1477104 A1 11/2004 |
| 2010/0023032 A1 1/2010 Granja Filho | EP | 1481642 A1 12/2004 |
| 2010/0036198 A1* 2/2010 Tacchino et al. ............. 600/106 | EP | 1493391 A1 1/2005 |
| 2010/0042045 A1 2/2010 Spivey | EP | 0848598 B1 2/2005 |
| 2010/0048990 A1 2/2010 Bakos | EP | 1281360 B1 3/2005 |
| 2010/0049190 A1 2/2010 Long et al. | EP | 1568330 A1 8/2005 |
| 2010/0049223 A1 2/2010 Granja Filho | EP | 1452143 B1 9/2005 |
| 2010/0056862 A1 3/2010 Bakos | EP | 1616527 A2 1/2006 |
| 2010/0057085 A1 3/2010 Holcomb et al. | EP | 1006888 B1 3/2006 |
| 2010/0057108 A1 3/2010 Spivey et al. | EP | 1629764 A1 3/2006 |
| 2010/0063538 A1 3/2010 Spivey et al. | EP | 1013229 B1 6/2006 |
| 2010/0076451 A1 3/2010 Zwolinski et al. | EP | 1721561 A1 11/2006 |
| 2010/0081877 A1 4/2010 Vakharia | EP | 1153578 B1 3/2007 |
| 2010/0087813 A1 4/2010 Long | EP | 1334696 B1 3/2007 |
| 2010/0113872 A1 5/2010 Asada et al. | EP | 1769766 A1 4/2007 |
| 2010/0121362 A1 5/2010 Clague et al. | EP | 1836971 A2 9/2007 |
| 2010/0130817 A1 5/2010 Conlon | EP | 1836980 A1 9/2007 |
| 2010/0130975 A1 5/2010 Long | EP | 1854421 A2 11/2007 |
| 2010/0131005 A1 5/2010 Conlon | EP | 1857061 A1 11/2007 |
| 2010/0152539 A1 6/2010 Ghabrial et al. | EP | 1875876 A1 1/2008 |
| 2010/0152609 A1 6/2010 Zwolinski et al. | EP | 1891881 A1 2/2008 |
| 2010/0152746 A1 6/2010 Ceniccola et al. | EP | 1902663 A1 3/2008 |
| 2010/0179510 A1 7/2010 Fox et al. | EP | 1477106 B1 6/2008 |
| 2010/0179530 A1 7/2010 Long et al. | EP | 1949844 A1 7/2008 |
| 2010/0191050 A1 7/2010 Zwolinski | EP | 1518499 B1 8/2008 |
| 2010/0191267 A1 7/2010 Fox | EP | 1709918 B1 10/2008 |
| 2010/0198005 A1 8/2010 Fox | EP | 1985226 A2 10/2008 |
| 2010/0198149 A1 8/2010 Fox | EP | 1994904 A1 11/2008 |
| 2010/0198244 A1 8/2010 Spivey et al. | EP | 1707130 B1 12/2008 |
| 2010/0198248 A1 8/2010 Vakharia | EP | 0723462 B1 3/2009 |
| 2010/0249700 A1 9/2010 Spivey | EP | 1769749 B1 11/2009 |
| 2010/0286791 A1 11/2010 Goldsmith | EP | 1493397 81 9/2011 |
| 2010/0298642 A1 11/2010 Trusty et al. | FR | 2731610 A 9/1996 |
| 2010/0312056 A1 12/2010 Galperin et al. | GB | 330629 A 6/1930 |
| 2010/0331622 A2 12/2010 Conlon | GB | 2335860 A 10/1999 |
| 2010/0331774 A2 12/2010 Spivey | GB | 2403909 A 1/2005 |
| 2011/0093009 A1 4/2011 Fox | GB | 2421190 A 6/2006 |
| 2011/0098694 A1 4/2011 Long | GB | 2443261 A 4/2008 |
| 2011/0098704 A1 4/2011 Long et al. | JP | 56-46674 4/1981 |
| 2011/0105850 A1 5/2011 Voegele et al. | JP | 63309252 A 12/1988 |
| 2011/0112434 A1 5/2011 Ghabrial et al. | JP | 4038960 A 2/1992 |
| 2011/0115891 A1 5/2011 Trusty | JP | 8-29698 A 2/1996 |
| 2011/0124964 A1 5/2011 Nobis | JP | 2000245683 A 9/2000 |
| 2011/0152609 A1 6/2011 Trusty et al. | JP | 2002-369791 A 12/2002 |
| 2011/0152610 A1 6/2011 Trusty et al. | JP | 2003-088494 A 3/2003 |
| 2011/0152612 A1 6/2011 Trusty et al. | JP | 2003-235852 A 8/2003 |
| 2011/0152858 A1 6/2011 Long et al. | JP | 2003-235852 A1 8/2003 |
| 2011/0152859 A1 6/2011 Long et al. | JP | 2004-33525 A 2/2004 |
| 2011/0152878 A1 6/2011 Trusty et al. | JP | 2004-065745 A 3/2004 |
| 2011/0152923 A1 6/2011 Fox | JP | 2005-121947 A 5/2005 |
| 2011/0160514 A1 6/2011 Long et al. | JP | 2005-261514 A 9/2005 |
| 2011/0190659 A1 8/2011 Long et al. | JP | 2006297005 A 11/2006 |
| 2011/0190764 A1 8/2011 Long et al. | | |

| | | | |
|---|---|---|---|
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/94082 A2 | 6/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

Cre™ Pulmonary Balloon Dilator; [online] URL: http://www.bostonscientific.com/Device.bsci?page=HCP_Overview&navRelId=1000.1003&method=D..., accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for Notes," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).
Weaver et al., "Theory of electroporation: A review," Bioelectrochemistry and Bioenergetics, 41, pp. 135-160 (1996).
Muller et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented at DDW Demonstrate Potential of Pure Notes Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
Octo Port Modular Laparoscopy System for Single Incision Access, Jan. 4, 2010; URL http://www.medgadget.com/archives/2010/01/octo_port_modular laparo...; accessed Jan. 5, 2010 (4 pages).
Hakko Retractors, obtained Aug. 25, 2009 (5 pages).
U.S. Appl. No. 12/277,957, filed Nov. 25, 2008.
U.S. Appl. No. 12/277,975, filed Nov. 25, 2008.
U.S. Appl. No. 12/332,938, filed Dec. 11, 2008.
U.S. Appl. No. 12/337,340, filed Dec. 17, 2008.

U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/635,298, filed Dec. 10, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du Feb. 24, 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastomosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastomosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis col. Rectum, (1963), vol. 5, pp. 98-101.
T. Hardy, Jr., M.D. et al., "A Biofragmentable Ring for Sutureless Bowel Anastomosis. An Experimental Study," Dis col. Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components—gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.

U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/130,023, filed May 30, 2008.
K. Sumiyama et al., "Endoscopic Caps," Tech. Gastrointest. Endosc., vol. 8, pp. 28-32, 2006.
D.B. Nelson, MD et al., "Endoscopic Hemostatic Devices," Gastrointestinal Endoscopy, vol. 54, No. 6, 2001, pp. 833-840.
U.S. Appl. No. 12/130,224, filed May 30, 2008.
International Preliminary Report on Patentability for PCT/US2009/054436, Mar. 1, 2011 (7 pages).
Zadno et al., "Linear Superelasticity in Cold-Worked NI-TI," Engineering Aspects of Shape Memory Alloys, pp. 414-419 (1990).
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.

* cited by examiner

ARTICULATING END CAP

BACKGROUND

Various embodiments are directed to surgical end caps, surgical instruments utilizing end caps and methods of using the same.

Minimally invasive procedures are desirable because such procedures can reduce pain and provide relatively quick recovery times as compared with conventional open medical procedures. Many minimally invasive procedures are performed with an endoscope. Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall.

Still less invasive treatments include those that are performed through insertion of an endoscope through a natural body orifice to a treatment site. Examples of this approach include, but are not limited to, cystoscopy, hysteroscopy, esophagogastroduodenoscopy, cholecystectomy, and colonoscopy. Many of these procedures employ the use of a flexible endoscope during the procedure. Flexible endoscopes often have a flexible, steerable articulating section near the distal end that can be controlled by the user by utilizing controls at the proximal end.

Some flexible endoscopes are relatively small (1 mm to 3 mm in diameter), and may have no integral working channel. Other flexible endoscopes, including gastroscopes and colonoscopes, have integral working channels having a diameter of about 2.0 to 3.7 mm for the purpose of introducing and removing medical devices and other accessory devices to perform diagnosis or therapy within the patient. Certain specialized endoscopes are available, such as large working channel endoscopes having a working channel of 5 mm in diameter, which can be used to pass relatively large accessories. Other specialized endoscopes include those having two working channels. A separate accessory channel can also be used in conjunction with a conventional endoscope to facilitate the introduction of additional surgical tools or accessories.

One disadvantage of known systems is the difficulty of precisely positioning and manipulating the distal end of a tool disposed through a working channel of an endoscope or through an accessory channel mated to an endoscope. Accordingly, a need exists for methods and devices for positioning and manipulating a tool.

FIGURES

The novel features of the various embodiments are set forth with particularity in the appended claims. The various embodiments, however, both as to organization and methods of operation, together with advantages thereof, may best be understood by reference to the following description, taken in conjunction with the accompanying drawings as follows.

DESCRIPTION

Various embodiments are directed to devices and methods for positioning a surgical tool including, for example, a tool introduced to a surgical site through a working channel of an endoscope. According to various embodiments, an articulating hollow end cap may be coupled to a distal end of the endoscope. In use, the endoscope with the articulating end cap may be introduced to a surgical site according to any suitable method. When the endoscope is in place, a distal rim of the end cap may be pressed against selected tissue at the surgical site. Various surgical tools may be extended through the working channel of the endoscope and through the hollow end cap to act on the selected tissue. According to various embodiments, the end cap may act as a shield, preventing the surgical tool from making unintended contact with tissue. Also, according to various embodiments, the clinician may change the orientation of the surgical tool relative to the selected tissue by articulating the end cap relative to the endoscope. For example, the end cap may rotate and/or pivot relative to the endoscope. When the end cap is held stationary against tissue, the rotation and/or pivoting due to articulation may be expressed by movement in the endoscope, thus changing the orientation of surgical tools relative to the end cap and the tissue.

Figure 1:
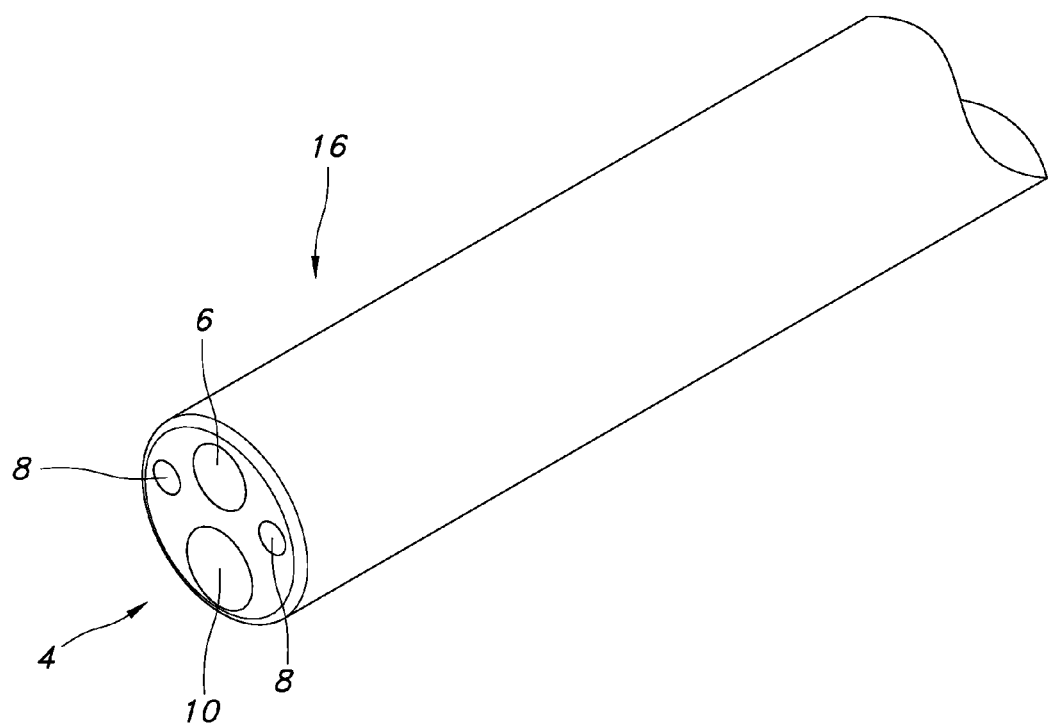
FIG. 1 illustrates one embodiment of a distal portion of an example endoscope that may be used with an end cap assembly.

FIG. 1 illustrates one embodiment of a distal portion of an example endoscope 16 that may be used with an end cap assembly, as described herein. The example endoscope 16 shown comprises a distal face 4, which defines the distal ends of illumination channels 8, an optical channel 6 and a working channel 10. The illumination channels 8 may comprise one or more optical fibers or other suitable waveguides for directing light from a proximally positioned light source (not shown) to the surgical site. The optical channel 6 may comprise one or more optical fibers or other suitable waveguides for receiving and transmitting an image of the surgical site proximally to a position where the image may be viewed by the clinician operating the endoscope 16. As described above, the working channel 10 may allow the clinician to introduce one or more surgical tools to the surgical site. Examples of such surgical tools include scissors, cautery knives, suturing devices, etc. It will be appreciated that the endoscope 16 is but one example of an endoscope that may be used in accordance with various embodiments. Endoscopes having alternate configurations of optical channels 6, illumination channels 8 and/or working channels 10 may also be used.

Figure 2:
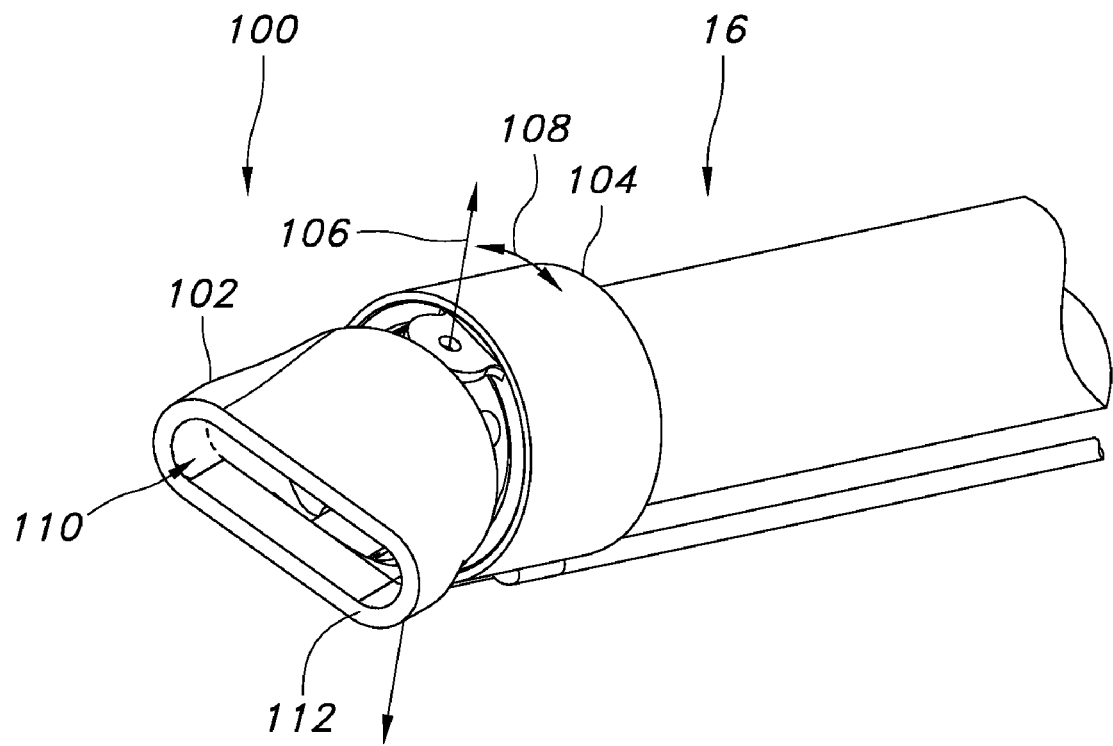
FIG. 2 illustrates one embodiment of the endoscope of FIG. 1 with an end cap assembly in place.

FIG. 2 illustrates one embodiment of the endoscope 16 with an end cap assembly 100 in place. The end cap assembly 100 may comprise a collar 104 and a hollow end cap 102. The hollow end cap 102 may comprise a distal rim 112 outlining an opening 110. The end cap 102 may be pivotable relative to the endoscope 16 about the axis 106 and also rotatable relative to the endoscope 16 about an axis perpendicular to the distal face 4 of the endoscope (e.g., as shown by arrow 108). The various components of the end cap assembly 100 may be made of any suitable material including, for example, a surgical grade plastic, a steel or other metal, etc. According to various embodiments, the end cap 102 may be transparent. This may allow the clinician to observe tissue through the end cap 102. It will be appreciated that in various embodiments, the end cap assembly 100 may also be used with an accessory channel or any other mechanism for providing surgical instruments to a, for example, endoscopic or laparoscopic surgical site.

Figure 3:
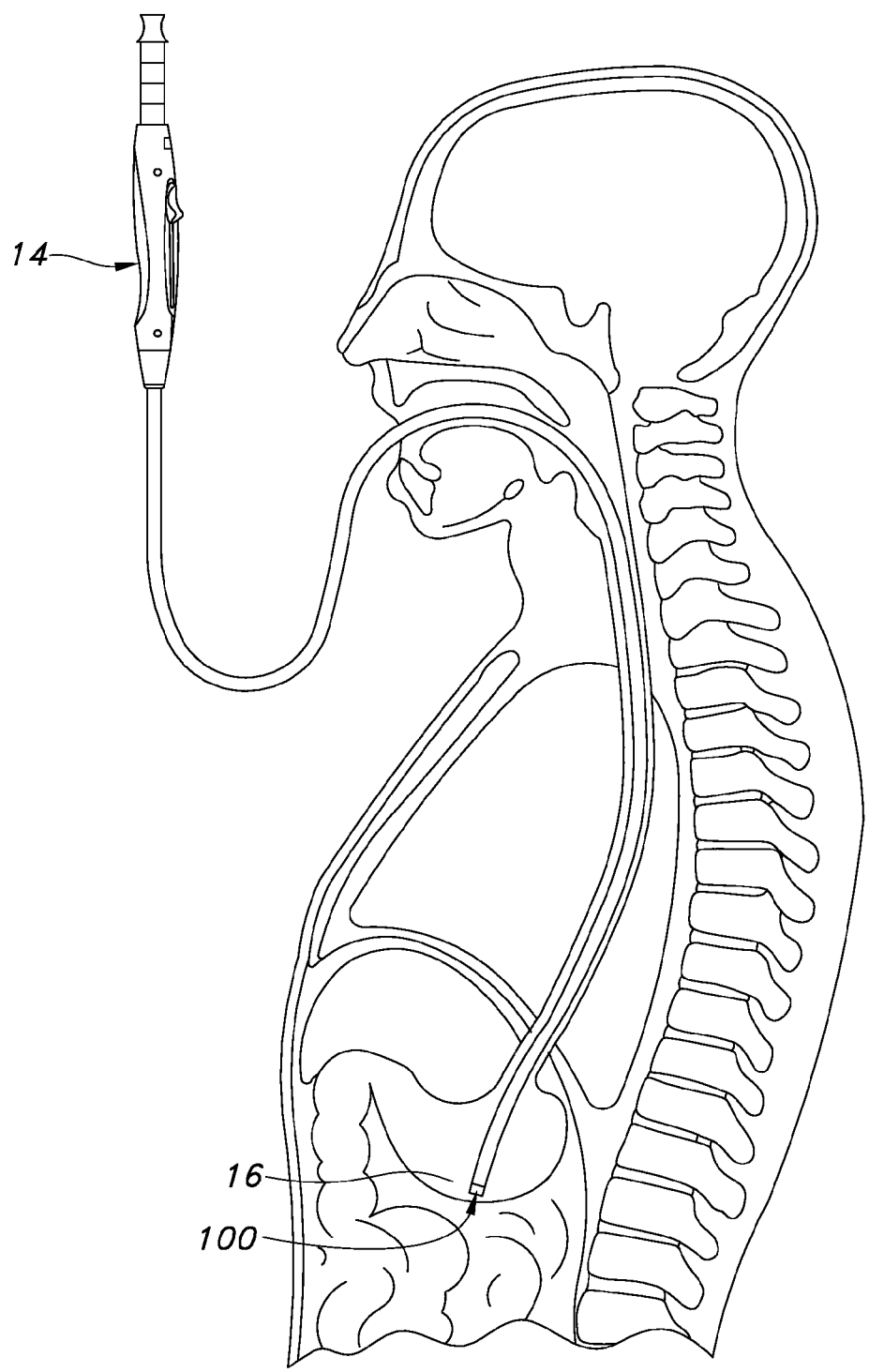
FIG. 3 illustrates one embodiment of a flexible endoscope (illustrated as a gastroscope) inserted into the upper gastrointestinal tract of a patient.

The endoscope 16 and end cap assembly 100 may be introduced to a surgical site according to any suitable method. For example, the endoscope 16 may be a rigid and/or flexible endoscope introduced via a trocar in a laparoscopic surgical environment or a flexible endoscope used in an endoscopic surgical environment. FIG. 3 illustrates one embodiment of a flexible endoscope 16 (illustrated here as a gastroscope) inserted into the upper gastrointestinal tract of a patient. According to various embodiments, the endoscope 16 may be a flexible endoscope and may be introduced via natural orifices and may be combined with trans-organ techniques. In one embodiment, Natural Orifice Translumenal Endoscopic Surgery (NOTES)™ techniques may be employed to introduce instruments into the patient and carry out the various procedures described hereinbelow. A NOTES™ technique is a minimally invasive therapeutic procedure that may be employed to treat diseased tissue or perform other therapeutic operations through a natural opening of the patient without making incisions in the abdomen. A natural opening may be the mouth, anus, and/or vagina. Medical implantable instruments may be introduced into the patient to the target area via the natural opening. In a NOTES™ technique, a surgeon inserts a flexible endoscope into one or more natural openings of the patient to view the target area using a camera. According to various embodiments, a steerable overtube may be inserted into the patient first. The endoscope and/or various other surgical tools may then be introduced to the surgical site through the overtube. During endoscopic surgery, the surgeon inserts surgical devices through one or more lumens or working channels of the endoscope 16 to perform various key surgical activities (KSA). These KSAs include forming an anastomosis between organs, repairing ulcers and other wounds, etc.

Figure 4A:
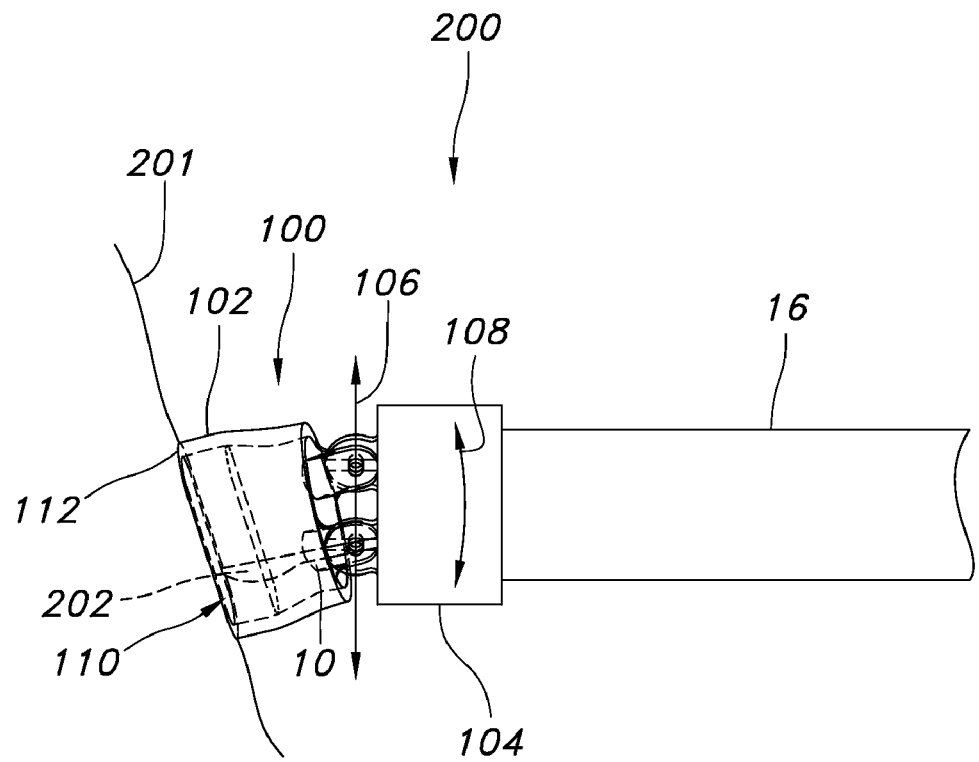
FIG. 4A illustrates a side view of one embodiment of the endoscope and end cap assembly of FIG. 2 with a distal rim of the end cap in use at a surgical site.
Figure 4B:
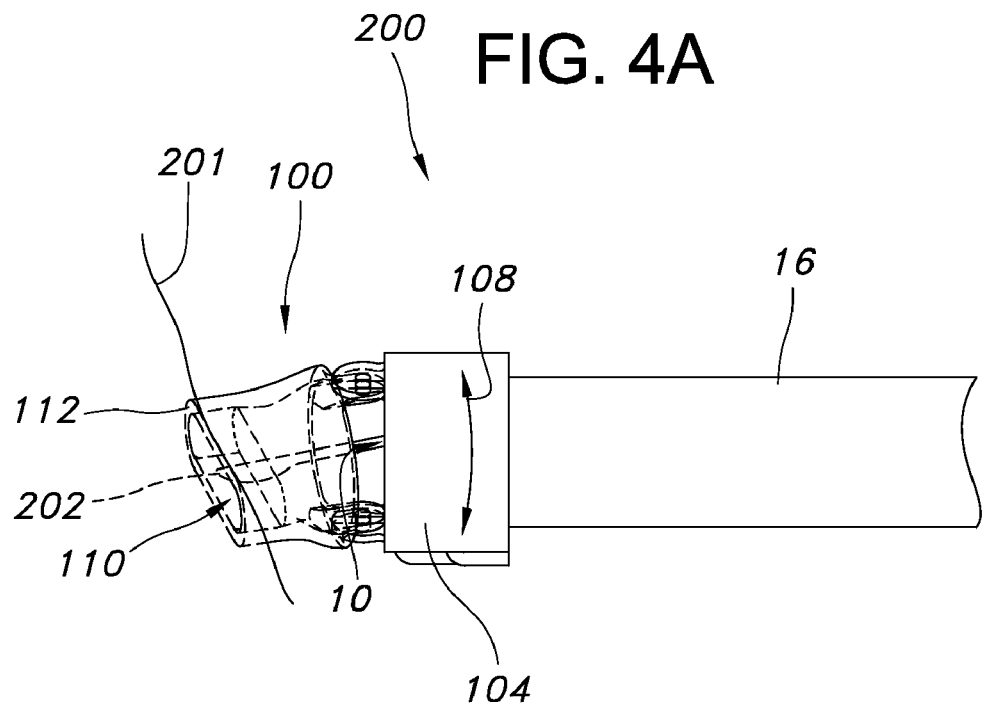
FIG. 4B illustrates a top view of one embodiment of the endoscope and end cap assembly of FIG. 2 with the distal rim of the end cap in use at the surgical site.

FIGS. 4A and 4B illustrate different perspectives of one embodiment of the endoscope 16 and cap assembly 100 in use at a surgical site. As shown, the distal rim 112 of the end cap 102 may be placed in contact with tissue to be acted upon. The clinician may apply some pressure forcing the end cap 102 against the tissue 201 to prevent the end cap 102 from slipping across the surface of the tissue 201. In this way, the distal rim 112 may be placed in secure contact with the tissue 201 so as to prevent and/or minimize slippage of the end cap 102 relative to the tissue 201. For example, according to various embodiments, the distal rim 112 may include features that allow it to more easily adhere to the tissue 201. For example, the distal rim 112 may be textured to increase the friction between the rim 112 and the tissue 201. Also, for example, the distal rim 112 may include an adhesive coating for increasing friction between the rim 112 and the tissue 201. The adhesive coating could be made from any suitable adhesive material including, for example, a polypropylene mesh, a hydrogel, a nanotextured polymer, etc.

With the end cap 102 securely placed in contact with tissue 201, a surgical tool 202 may be introduced to the surgical site via the working channel 10 and the opening 110 of the end cap 102. The clinician may change the orientation of the surgical tool 202 relative to the tissue by articulating the end cap 102 relative to the distal face 4 of the endoscope 16. For example, the end cap 102 may pivot about axis 106 and/or rotate according to arrow 108. Pivoting the end cap 102 about the axis 106 may tend to sweep the surgical tool 202 across the tissue 201 accessible through the opening 110. Rotating the end cap 102 about the endoscope 16 may also change the orientation of the surgical tool 202 relative to the tissue. Also, the end cap 102 may serve to limit the portion of the tissue 201 that the surgical tool 202 is able to contact. Accordingly, the shape of the opening 110 may be selected based on the surgical task to be performed. For example, the elongated ovaloid shaped opening 110 shown in FIGS. 4A and 4B may allow the clinician to sweep the surgical tool 202 across the tissue 201 by pivoting the end cap 102. In some surgical procedures, the endoscope 16 and end cap assembly 100 may be retracted slightly from the tissue 201, articulated, and then re-applied to the tissue 201.

Various different mechanisms and methods may be used to bring about articulation of the end cap assembly 100. For example, according to various embodiments, the end cap assembly 100 may be passively articulated using a steering mechanism of a steerable endoscope. A steerable endoscope is a flexible endoscope including a steering mechanism that allows a clinician to bend or otherwise direct a distal portion of the endoscope in a desired direction relative to the remainder of the endoscope. This may allow the clinician to maneuver or "steer" the endoscope through the patient's body to a surgical site. A steerable endoscope may use any suitable steering mechanism. For example, according to various embodiments, a steerable endoscope may employ four 90° spaced quadrant cables which interact mechanically with a series of vertebrated or specifically profiled rings located adjacent to the distal end of the endoscope. Controls, such as joysticks, wheels, stepper motors, etc., may allow the clinician to alternatively tension and relax the cables to bend and deflect the rings, causing the distal portion of the endoscope to articulate. One example of a steerable endoscope is provided in U.S. Pat. No. 4,207,873 to Kruy, which is incorporated herein by reference in its entirety.

Figure 5:
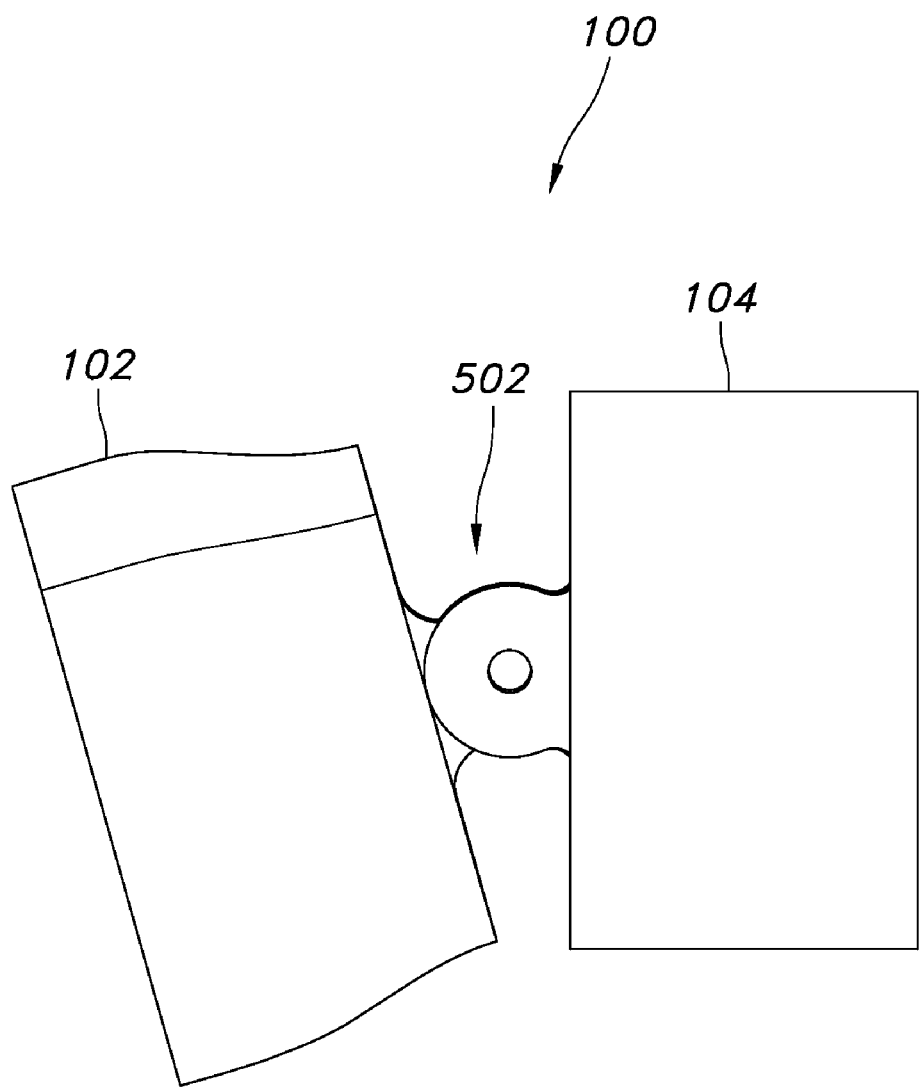
FIG. 5 illustrates one embodiment of the end cap assembly of FIG. 2 where the end cap is coupled to a collar via a pin and loop hinge.
Figure 6:
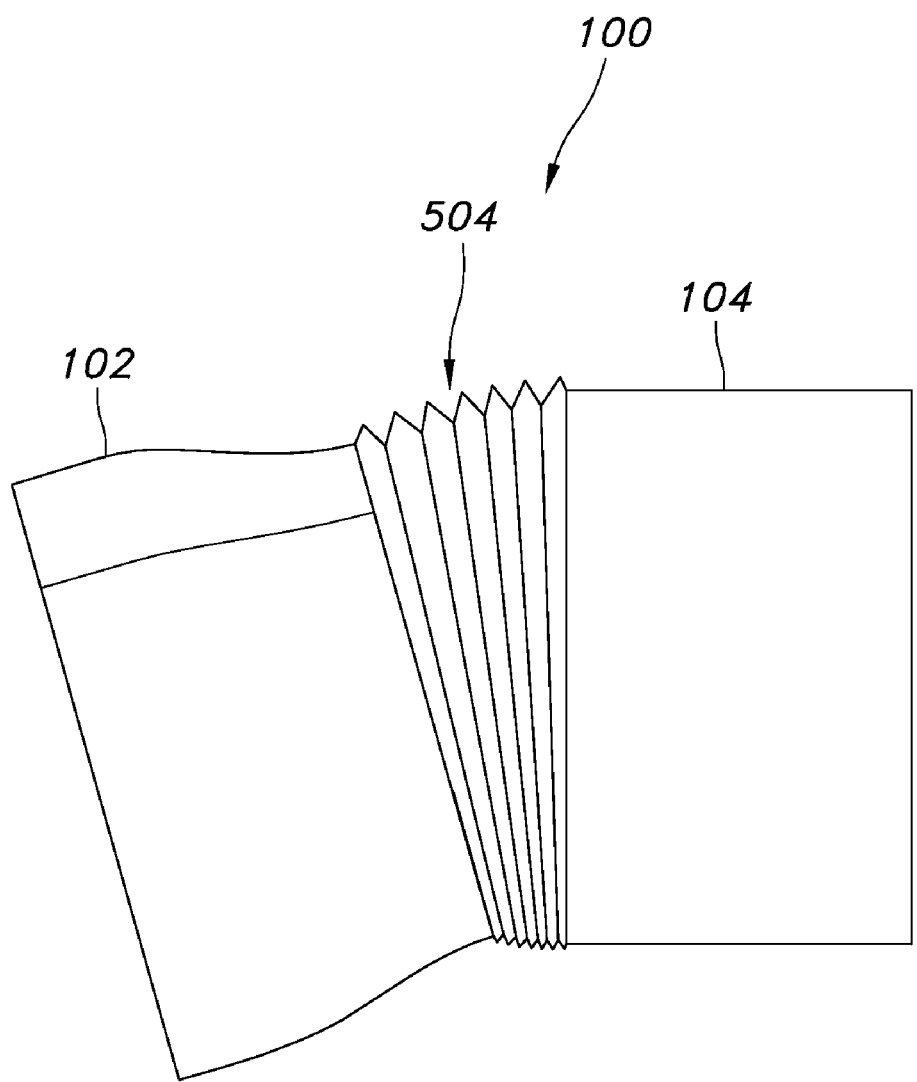
FIG. 6 illustrates another embodiment of the end cap assembly of FIG. 2 where the end cap is coupled to the collar via a hinge made of flexible and/or elastic material.

The steering function of a steerable endoscope may be used to cause the end cap 102 and collar 104 to pivot about the axis 106. For example, the end cap 102 may be coupled to the collar 104 via a hinge that allows the end cap 102 to pivot freely relative to the collar 104 about the axis 106. When the end cap 102 is secured against tissue 201 (shown in FIGS. 4A and 4B) the clinician may steer the distal portion of the endoscope from side-to-side, causing the endoscope 16 and the collar 104 to pivot about the hinge relative to the stationary end cap 102, and thus articulating the end cap 102 about the axis 106. Any suitable type of mechanical hinge may be used. For example, FIG. 5 illustrates one embodiment of the end cap assembly 100 where the end cap 102 is coupled to the collar 104 via a pin and loop hinge 502. FIG. 6 illustrates another embodiment of the end cap assembly 100 where the hinge 502 is replaced with a hinge 504 made of a flexible and/or elastic material and/or material folded in an accordion-like manner to have flexible and/or elastic properties.

According to various embodiments, rotation of the end cap 102 according to the arrow 108 may also be initiated passively by manipulating the endoscope 16. For example, the collar 104 may be rotatably coupled to the endoscope 16 in a manner that allows it to freely rotate according to the arrow 108. When the end cap 102 is in contact with tissue, the clinician may rotate the endoscope 16. This may bring about rotation of the end cap 102 relative to the endoscope 16.

Figure 7A:
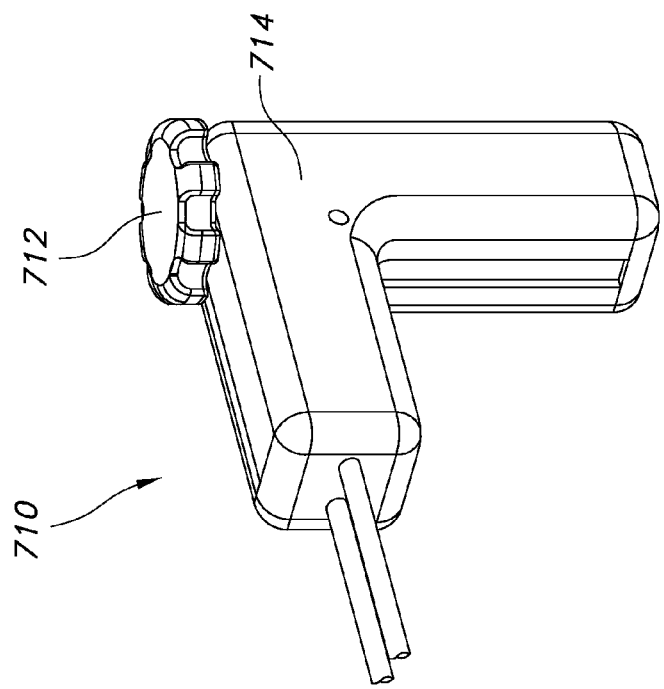
FIG. 7A illustrates one embodiment of the end cap assembly of FIG. 2 including a translating mechanism for actively pivoting the end cap.
Figure 7A:
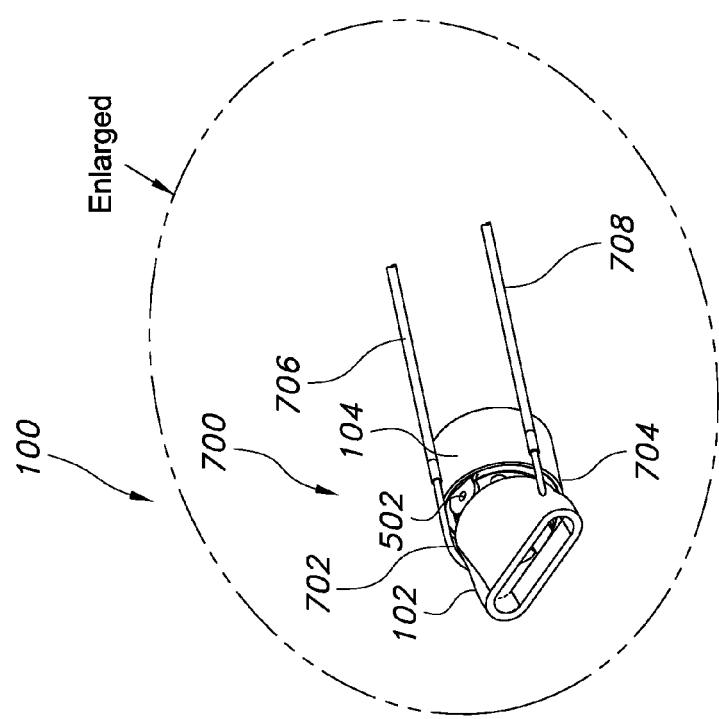

In some embodiments, the end cap 102 may be actively articulated by the clinician. For example, FIG. 7A illustrates one embodiment of the end cap assembly 100 including a translating mechanism 700 for actively pivoting the end cap 102. The translating mechanism 700 may comprise one or more pieces of flexible material including, for example, cables, ropes, cords, etc. having two distal ends 702, 704. The distal ends 702, 704 may be coupled to respective sides of the end cap 102. The translating mechanism may be slidably disposed within first and second tubes 706, 708, which may extend proximally to an actuating device 710.

Figure 7B:
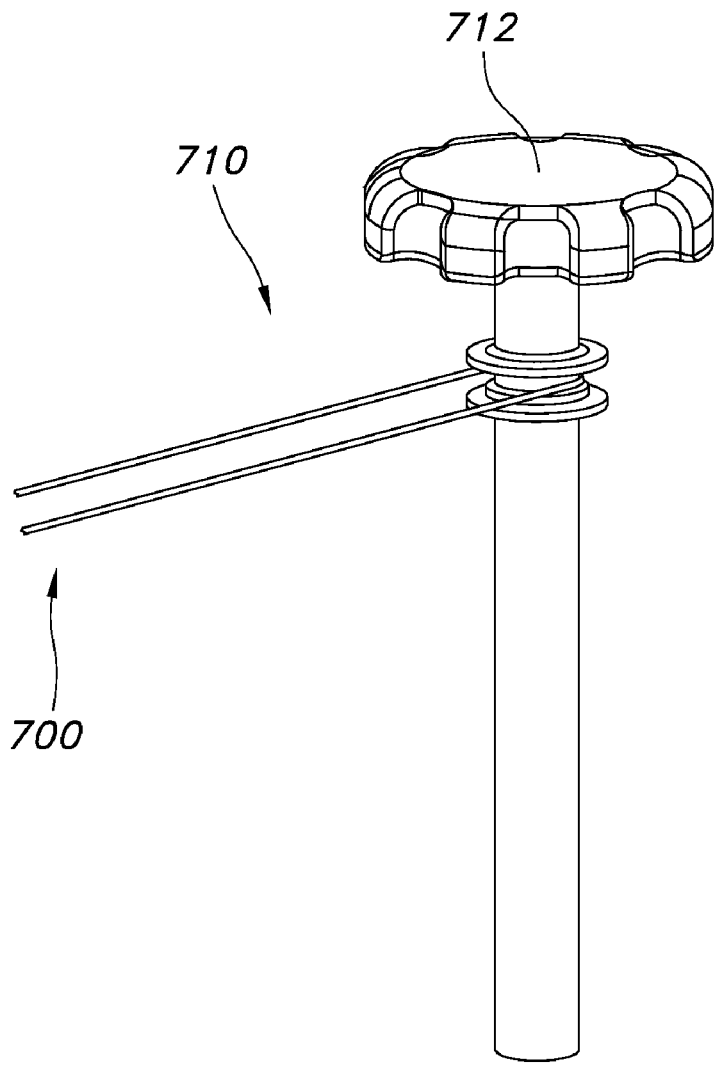
FIG. 7B illustrates one embodiment of an actuating device comprising a knob.

The actuating device 710 may be operable to retract one of the distal ends 702, 704 while extending the other. In this way, the end cap 102 may pivot toward the distal end being retracted. As shown in FIG. 7A, distal end 704 is retracted, while distal end 702 is extended. Likewise, if the distal end 702 were to be retracted and the distal end 704 were to be extended, the end cap 102 would pivot toward the top of the figure. FIG. 7B illustrates one embodiment of the actuating device 710 comprising a knob 712. The knob 712 may be rotatably coupled to a handle 714 of the actuating device. According to various embodiments, the translating mechanism 700 may be wrapped around the knob 712, such that when the knob 712 is twisted, one distal end of the translating mechanism is retracted while the other is extended. It will be appreciated that this is just one example of an actuating device that may be used with the end cap assembly 100, and that any device capable of retracting one distal end 702, 704 while extending the other may be used.

Figure 8A:
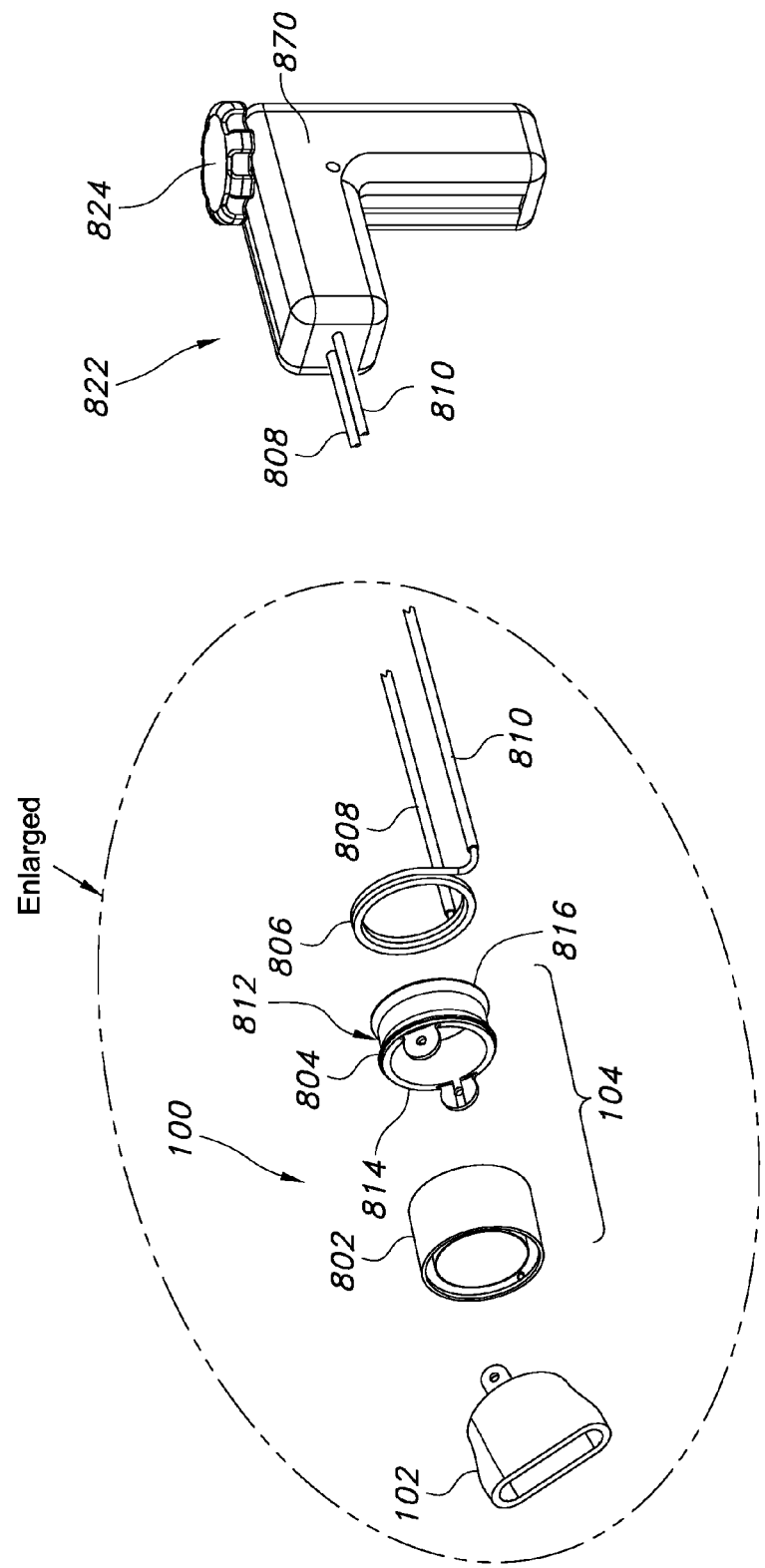
FIG. 8A illustrates an exploded view of one embodiment of the end cap assembly of FIG. 2 including an elongate translating mechanism for rotating the end cap.
Figure 8B:
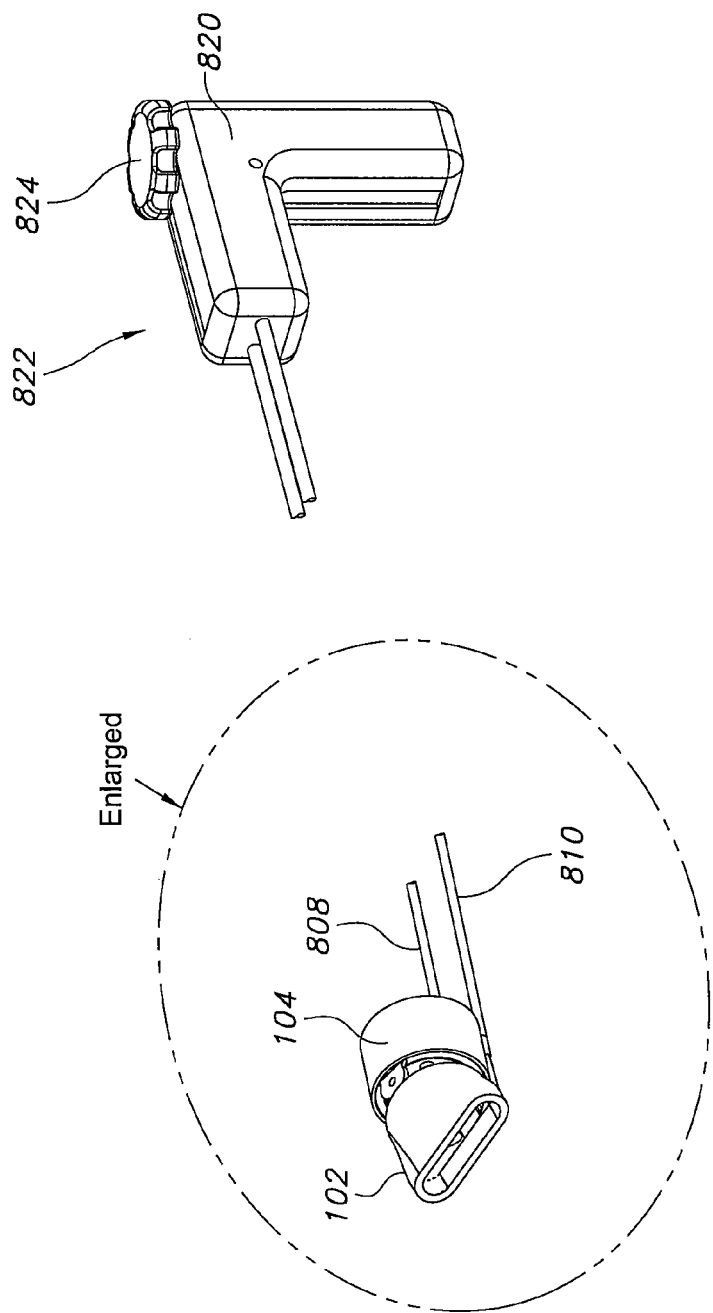
FIG. 8B illustrates a constructed view of the embodiment shown in FIG. 8A.

According to various embodiments, the end cap 102 may also be actively rotated about the endoscope 16. For example, FIG. 8A illustrates an exploded view of one embodiment of the end cap assembly 100 including an elongate translating mechanism 806 for rotating the end cap 102. FIG. 8B illustrates a constructed view of the same embodiment. As shown in FIG. 8A, the collar 104 may comprise an outer sleeve 802 and an inner sleeve 804. The inner sleeve 804 may be rotatably coupled to the endoscope 16. For example, the inner sleeve 804 may comprise bearings (not shown) and/or other suitable mechanisms allowing it to be coupled to the endoscope 16, but also rotatable about the exterior of the endoscope 16. The translating mechanism 806 may be slidably disposed within first and second elongate tubes 808, 810 that may be coupled to the outer sleeve 802 at a distal end, and that are coupled to a handle 820 at a proximal end. A distal end of the translating mechanism 806 is coupled to the inner sleeve 804, and a proximal end extends into a handle 820 and is operatively associated with the actuating mechanism 822. The actuating mechanism 822 may be effective to cause the translating mechanism 806 to apply a rotational force to the inner sleeve 804 to rotate the inner sleeve 804 and end cap 102. While not shown, one or more clamps can be provided to secure the elongate tubes 808, 810 to the endoscope.

In an example embodiment, the translating mechanism 806 may comprise an elongate flexible cable that is wound around the inner sleeve 804. Thus, the inner sleeve can include a seating surface 812 for receiving the cable. While the shape of the seating surface 812 can vary, in an exemplary embodiment, the inner sleeve 804 may have a concave seating surface 812 with opposed flanges 814, 816 that extend outward from the inner sleeve 804. The concave shape of the seating surface 812 can pull the translating mechanism 806 toward the mid-portion of the surface as the inner sleeve 804 is rotated, thereby preventing the translating mechanism 806 from bunching or jumping over the opposed flanges 814, 816, becoming entangled, or otherwise inhibiting rotation of the inner sleeve 804.

Figure 9A:
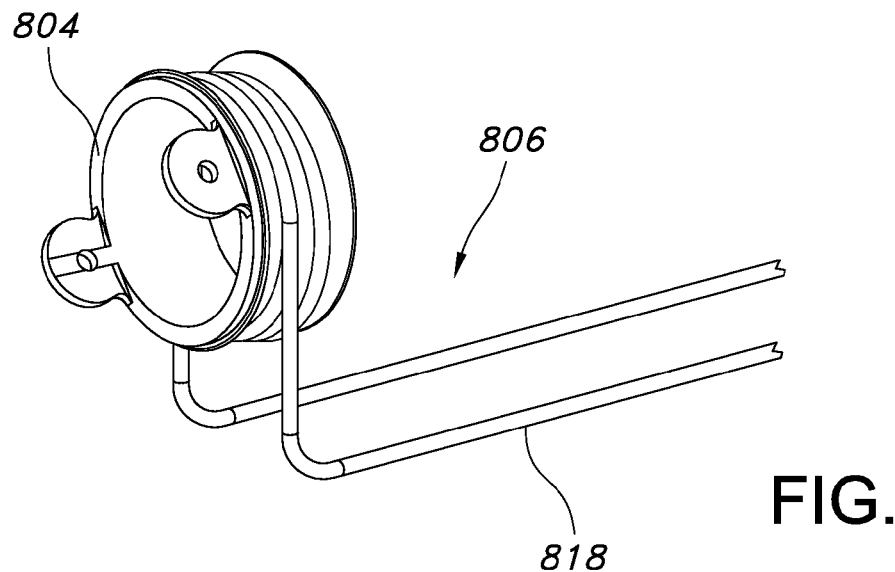
FIG. 9A illustrates one embodiment of the continuous cable loop shown in FIG. 8A wrapped around an inner sleeve.
Figure 9B:
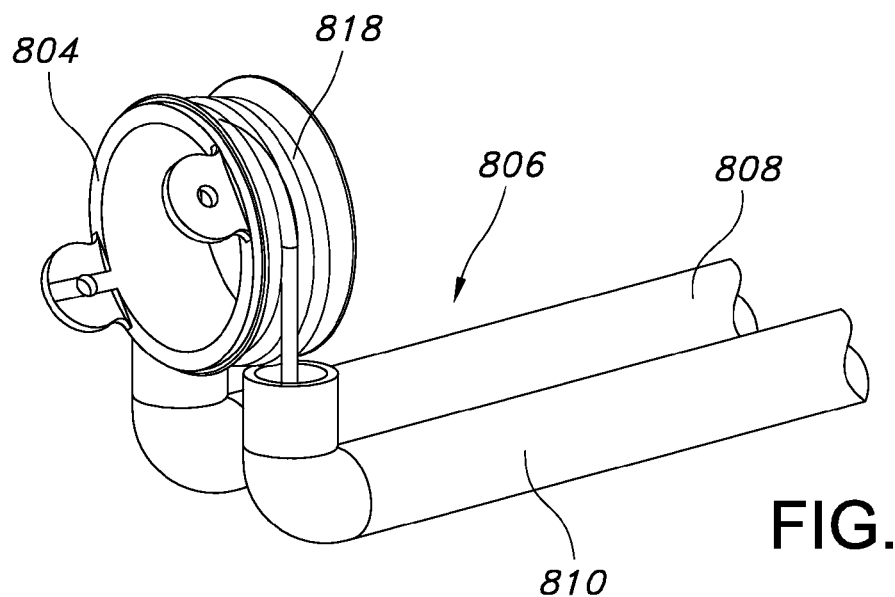
FIG. 9B illustrates another embodiment of the continuous cable loop of FIG. 8A wrapped around the inner sleeve and slidably disposed through first and second elongate tubes.

The translating mechanism 806 can also have a variety of configurations, but as indicated above, in an example embodiment, the translating mechanism 806 is in the form of a single, continuous cable loop 818 having a distal portion that is wound around the inner sleeve 804. FIG. 9A illustrates one embodiment of the continuous cable loop 818 wrapped around the inner sleeve 804. FIG. 9B illustrates another embodiment of the continuous cable loop 818 wrapped around the inner sleeve 804 and slidably disposed through the first and second elongate tubes 808, 810. A proximal portion of the cable 818 can be operatively associated with the actuating mechanism 822 which will be discussed in more detail below. While the device is shown with a cable actuator 818, a person skilled in the art will appreciate that the translating mechanism 806 can also be in the form of a wire, braided rope, or other flexible cord. The translating mechanism 806 can be made from any flexible material suitable for being wound around the inner sleeve 804. In use, the translating mechanism 806 can slide along the longitudinal axis of the device, and the axial force can be converted to a rotational force to cause the inner sleeve 804, and thus the end cap 102, to rotate.

Figure 10:
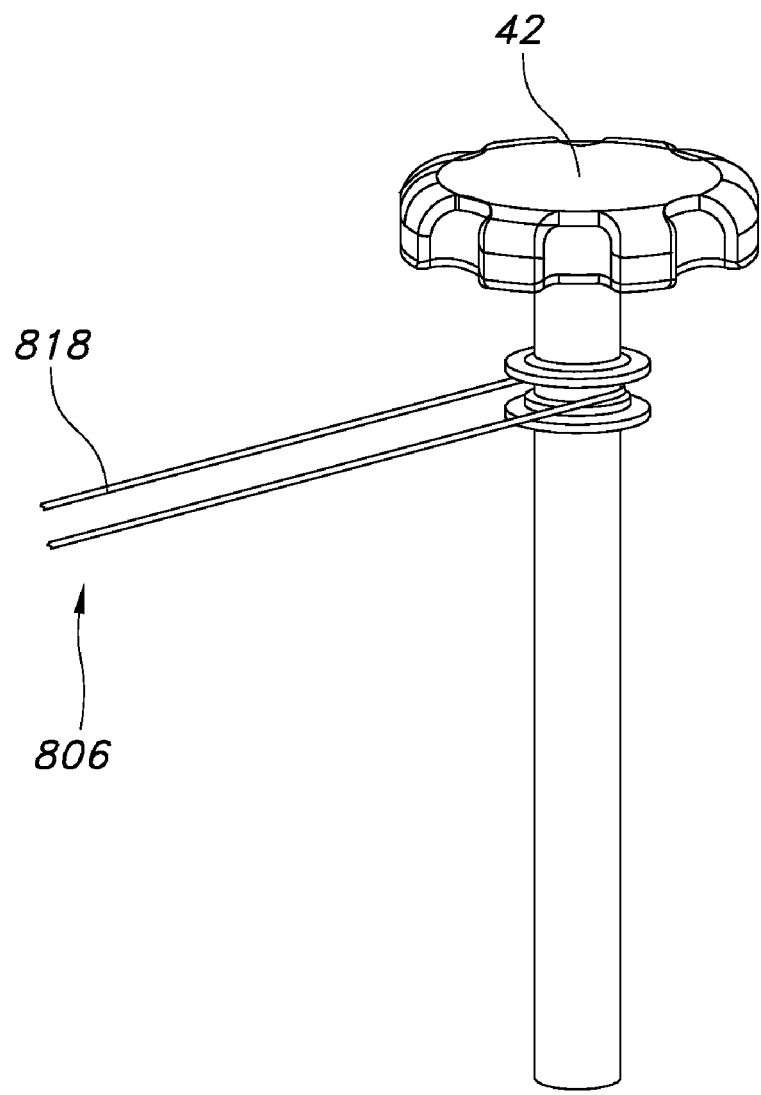
FIG. 10 illustrates one embodiment of an actuating mechanism in the form of a knob rotatably coupled to a handle or housing for actuating the translating mechanism shown in FIG. 8A.

The actuating mechanism 822 of the device is preferably configured to apply a translational force to the translating mechanism 806 to slide the translating mechanism 806 along the longitudinal axis of the device. FIG. 10 illustrates one embodiment of an actuating mechanism 822 in the form of a knob 824 rotatably coupled to a handle or housing 820 for actuating the translating mechanism 806. In the illustrated embodiment, the translating mechanism 806 (e.g., the cable actuator 818) is wound around the knob 824 such that rotation of the knob 824 will apply a rotational force to the translating mechanism 806 to cause it to translate axially through the tubes 808, 810. To increase the friction between the knob 824 and the mechanism 806 and to prevent the translating mechanism 806 from slipping, the knob 824 can include a sticky or textured surface and/or the translating mechanism 806 can be wound around the knob 824 multiple times.

In various embodiments, the endoscope 16 used in conjunction with the end cap assembly 100 may be a flexible endoscope, such as a GIF-100 model available from Olympus Corporation, for example. In at least one such embodiment, the endoscope 16, which may be a laparoscope, or a thoracoscope, for example, may be introduced into the patient trans-anally through the colon, the abdomen via an incision or keyhole and a trocar, or trans-orally through the esophagus, for example. These devices may assist the surgeon to guide and position the end cap assembly near the tissue treatment region to treat diseased tissue on organs such as the liver, for example. In another embodiment, these devices may be positioned to treat diseased tissue near the gastrointestinal (GI) tract, esophagus, and/or lung, for example. In various embodiments, the endoscope may comprise a flexible shaft where the distal end of the flexible shaft may comprise a light source, a viewing port, and at least one working channel. In at least one such embodiment, the viewing port may transmit an image within its field of view to an optical device such as a charge coupled device (CCD) camera within the endoscope, for example, so that an operator may view the image on a display monitor (not shown).

It will be appreciated that the terms "proximal" and "distal" are used herein with reference to a clinician manipulating an end of an instrument extending from the clinician to a surgical site (e.g., through a trocar, through a natural orifice, through an open surgical site, etc.). The term "proximal" refers to the portion closest to the clinician, and the term "distal" refers to the portion located away from the surgeon. It will be further appreciated that for conciseness and clarity, spatial terms such as "vertical," "horizontal," "up," and "down" may be used herein with respect to the drawings. However, surgical instruments are used in many orientations and positions, and these terms are not intended to be limiting and absolute.

While several embodiments have been illustrated and described, and while several illustrative embodiments have been described in considerable detail, the embodiments are not intended to restrict or in any way limit the scope of the appended claims to such detail. Additional advantages and modifications may readily appear to those skilled in the art. Those of ordinary skill in the art will readily appreciate the different advantages provided by these various embodiments.

While several embodiments have been described, it should be apparent, however, that various modifications, alterations and adaptations to those embodiments may occur to persons skilled in the art with the attainment of some or all of the advantages of the embodiments. For example, according to various embodiments, a single component may be replaced by multiple components, and multiple components may be replaced by a single component, to perform a given function or functions. This application is therefore intended to cover all such modifications, alterations and adaptations without departing from the scope of the appended claims.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the embodiments described herein will be processed before surgery. First a new or used instrument is obtained and, if necessary, cleaned. The instrument may then be sterilized. In one sterilization technique, the instrument is placed in a closed and sealed container, such as a plastic or TYVEK® bag. The container and instrument are then placed in a field of radiation that may penetrate the container, such as gamma radiation, x-rays, or higher energy electrons. The radiation kills bacteria on the instrument and in the container. The sterilized instrument may then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The embodiments are not to be construed as limited to the particular embodiments disclosed. The embodiments are therefore to be regarded as illustrative rather than restrictive. Variations and changes may be made by others without departing from the scope of the claims. Accordingly, it is expressly intended that all such equivalents, variations and changes that fall within the scope of the claims be embraced thereby.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical applications to thereby enable one of ordinary skill in the art to utilize the various embodiments and with various modifications as are suited to the particular use contemplated. It is intended that the claims submitted herewith define the overall scope.

What is claimed is:

1. A surgical device comprising:
 a collar configured to fit over a distal face of an endoscope, wherein the collar is rotatable about a longitudinal axis of the endoscope;
 a flexible, elongate translating mechanism coupled to the collar and extending proximally from the collar, wherein applying a linear force to the translating mechanism causes the translating mechanism to exert a rotational force on the collar;
 a hollow cap coupled to a distal end of the collar and covering at least a portion of the distal face of the endoscope, wherein the cap is pivotable relative to the collar in a plane parallel to the axis, wherein the cap has a first open end configured to face the distal face of the endoscope and a second open end configured to face distally.

2. The surgical device of claim 1, wherein the cap is pivotable relative to the collar about a hinge.

3. The surgical device of claim 1, wherein the cap is coupled to the distal end of the collar via a flexible member and wherein the cap is pivotable relative to the collar about the flexible member.

4. The surgical device of claim 1, wherein the translating mechanism comprises a first coil positioned around the collar, and wherein the first coil comprises at least one wire end extending proximally from the collar.

5. The surgical device of claim 4, wherein the collar comprises an inner sleeve and an outer sleeve, wherein the first coil is positioned around the inner sleeve, and wherein the outer sleeve is positioned over the inner sleeve.

6. The surgical device of claim 4, further comprising an actuating mechanism positioned proximally from the collar, wherein the actuating mechanism is coupled to the translating mechanism and is configured to apply a linear force to the translating mechanism.

7. The surgical device of claim 6, wherein the actuating mechanism comprises a proximal handle comprising a rotatable knob, and wherein the translating mechanism is coupled to the rotatable knob such that rotation of the knob causes a linear force to be applied to the translating mechanism.

8. The surgical device of claim 1, wherein the first open end defines an opening of a size approximately corresponding to the size of the distal face of the endoscope.

9. The surgical device of claim 1, wherein the second open end defines an opening having a width greater than its length.

10. The surgical device of claim 9, wherein the opening is an oval.

11. The surgical device of claim 1, wherein a distally facing surface of the second open end comprises a friction-enhancing surface.

12. The surgical device of claim 11, wherein the distally facing surface of the second open end defines a frictional texture.

13. The surgical device of claim 11, wherein the distally facing surface of the second open end comprises a tacky material.

14. The surgical device of claim 1, further comprising a second translating device comprising a first end extending proximally from a first side of the cap and a second end extending proximally from a second side of the cap, wherein exerting a proximally directed force on the first end causes the cap to pivot in a first direction and exerting a proximally directed force on the second end causes the cap to pivot in a second direction opposite the first direction.

15. The surgical device of claim 1, further comprising a proximally positioned actuating device comprising a handle and a knob, wherein rotating the knob in a first direction causes the proximally directed force to be exerted on the first end and rotating the knob in the second direction causes the proximally directed force to be exerted on the second end.

16. The surgical device of claim 1, wherein the cap is made from a material selected from the group consisting of a plastic and a metal.

17. A surgical device comprising:
a collar configured to fit over a distal face of an accessory channel, wherein the collar is rotatable about a longitudinal axis of the accessory channel;
a flexible, elongate translating mechanism coupled to the collar and extending proximally from the collar, wherein applying a linear force to the translating mechanism causes the translating mechanism to exert a rotational force on the collar;
a hollow cap coupled to a distal end of the collar and covering at least a portion of the distal face of the endoscope, wherein the cap is pivotable relative to the collar in a plane parallel to the axis, wherein the cap has a first open end configured to face the distal face of the accessory channel and a second open end configured to face distally.

18. A surgical device comprising:
a collar configured to fit over a distal face of an endoscope, wherein the collar is rotatable about a longitudinal axis of the endoscope; and
a hollow cap coupled to a distal end of the collar and covering at least a portion of the distal face of the endoscope, wherein the cap is pivotable relative to the collar in a plane parallel to the axis, wherein the cap has a first open end configured to face the endoscope and a second open end configured to face distally.

19. A method of using an endoscope, the endoscope comprising a rotatable collar positioned over a distal face of an endoscope, wherein the collar is rotatable about the distal face of the endoscope; a flexible, elongate translating mechanism coupled to the collar and extending proximally from the collar, wherein applying a linear force to the translating mechanism causes the translating mechanism to exert a rotational force on the rotatable collar; and a hollow cap coupled to a distal end of the collar, wherein the cap is pivotable relative to the collar in a plane parallel to the axis, wherein the cap has a proximally-facing open end configured to face the endoscope and a distally-facing open end, the method comprising:
introducing a distal portion of the endoscope to a surgical site;
extending the endoscope to bring the distally-facing open end of the cap into contact with tissue;
rotating the collar to change the orientation of the distal face of the endoscope relative to the tissue; and
pivoting the cap to change the orientation of the distal face of the endoscope relative to the tissue.

20. The method of claim 19, wherein rotating the collar comprises applying a linear force to the translating mechanism.

21. The method of claim 19, wherein pivoting the cap comprises steering a distal portion of the endoscope while the distally-facing open end of the cap is in contact with the tissue.

22. The method of claim 19, further comprising extending a surgical tool from a working channel of the endoscope and acting on the tissue with the surgical tool.

23. The method of claim 22, wherein the surgical tool is selected from the group consisting of scissors, a cautery knife and a suturing device.

24. The method of claim 19, wherein rotating the collar causes a change in the orientation of the surgical tool relative to the tissue.

25. The method of claim 19, wherein pivoting the cap causes a change in the orientation of the surgical tool relative to the tissue.

26. The method of claim 19, wherein the pivoting is performed while the surgical tool is in contact with the tissue.

27. The method of claim 19, wherein pivoting the cap comprises exerting a force on a second translating device coupled to a first side of the hollow cap.

28. The method of claim 19, further comprising introducing an overtube to the surgical site, wherein introducing the distal end of the endoscope to the surgical site comprises extending the endoscope through the overtube.

29. The method of claim 19, wherein introducing the distal portion of the endoscope to the surgical site comprises extending the distal portion of the endoscope through at least one natural orifice.

30. The method of claim 19, wherein the collar is rotatable about a longitudinal axis of the endoscope.

31. The method of claim 19, wherein the hollow cap covers at least a portion of the distal face of the endoscope, and wherein the proximally-facing open end is configured to face the distal face of the endoscope.

32. The method of claim 19:
wherein the collar is rotatable about a longitudinal axis of the endoscope;
wherein the hollow cap covers at least a portion of the distal face of the endoscope; and
wherein the proximally-facing open end is configured to face the distal face of the endoscope.

* * * * *